United States Patent
Kim et al.

(10) Patent No.: US 8,143,028 B2
(45) Date of Patent: Mar. 27, 2012

(54) BACILLUS LICHENIFORMIS B1, ALKALOPHILIC ENZYME SOLUTION AND METHOD OF PRODUCING THE SAME

(75) Inventors: Han Bok Kim, Chungcheongnam-do (KR); Jae Sung Hwang, Chungcheongnam-do (KR)

(73) Assignee: Hoseo University Academic Cooperation Foundation, Chungcheongnam-do (KR)

( * ) Notice: Subject to any disclaimer, the term of this patent is extended or adjusted under 35 U.S.C. 154(b) by 238 days.

(21) Appl. No.: 12/242,234

(22) Filed: Sep. 30, 2008

(65) Prior Publication Data

US 2009/0317871 A1    Dec. 24, 2009

(30) Foreign Application Priority Data

Jun. 19, 2008 (KR) .................. 10-2008-0057860

(51) Int. Cl.
*C12P 21/04* (2006.01)
*A61K 38/47* (2006.01)
*C12N 9/42* (2006.01)

(52) U.S. Cl. ............... 435/71.2; 424/94.61; 435/209

(58) Field of Classification Search ............ 435/71.2, 435/209; 424/94.61
See application file for complete search history.

(56) References Cited

FOREIGN PATENT DOCUMENTS

| KR | 10-0368183 | * | 5/2000 |
| KR | 10-0368183 | * | 7/2000 |

OTHER PUBLICATIONS

Bowie et al Science, 1990, 247:1306-1310.*
Shikata et al 1990 Agric. Biol. Chem., vol. 54(1) pp. 91-96.*
Bowie et al (Science, 1990, 247:1306-1310).*
Hwang et al Mar. 2008 Korean Journal of Microbiology vol. 44, No. 1 pp. 69-73) (see English abstract).*

* cited by examiner

*Primary Examiner* — Gary Nickol
*Assistant Examiner* — Nina Archie
(74) *Attorney, Agent, or Firm* — Saliwanchik, Lloyd & Eisenschenk (57) ABSTRACT

The present invention relates to *Bacillus licheniformis* B1 strain, alkalophilic enzyme solution and a method for preparing the same, in particular the method for producing cellulase demonstrating optimal activity at pH 10-13 by using *Bacillus licheniformis* B1 strain. The enzyme produced by the method of the present invention and the enzyme solution containing the same have excellent enzyme activity in alkali condition, so that they can be effectively applied in diverse uses including the production of detergent or bio-fuel.

17 Claims, 5 Drawing Sheets

|  | 10 | 20 | 30 | 40 | 50 | 60 | 70 | 80 | 90 |
|---|---|---|---|---|---|---|---|---|---|
| B1, | MMRRRKRSDM | KRSISIFITC | LLITVLTMSG | LPASPASAAG | TKTPVAKNGQ | LSIKGTQLVN | RDGKAIQLKG | ISSHGLQWYG | DFVNKDSLKW |
| DLG, | MMRRRKRSDM | KRSISIFITC | LLAVLTMGG | LLPSPASAAG | TKTPVAKNGQ | LSIKGTQLVN | RDGKAIQLKG | ISSHGLQWYG | DFVNKDSLKW |
| K11, | M | KRSISIFITC | LLAVLTMGG | LLPSPASAAG | TKTPVAKNGQ | LSIKGTQLVN | RDGKAIQLKG | ISSHGLQWYG | DFVNKDSLKW |
| Umas | M | KRSISIFITC | LLAVLTMGG | LLPSPASAAG | TKTPVAKNGQ | LSIKDTQLVN | RDGKAIQLKG | ISSHGLQWYG | DFVNKDSLKW |
| Consensus | M | KRSISIFITC | LLaVLTMgG | LlpSPASAAG | TKTPVAKNGQ | LSIKgTQLVN | RDGKAIQLKG | ISSHGLQWYG | DFVNKDSLKW |

|  | 100 | 110 | 120 | 130 | 140 | 150 | 160 | 170 | 180 |
|---|---|---|---|---|---|---|---|---|---|
| B1, | LRDDWGITVF | RAAMYTADGG | YIDNPSVKNK | VKEAVETAKE | LGIYVIIDWH | ILNDGNPNQN | KEKAKEFFKE | MSSLYGNTPN | VIYEIANEPN |
| DLG, | LRDDWGITVF | RAAMYTADGG | YIDNPSVKNK | VKEAVEAAKE | LGIYVIIDWH | ILNDGNPNQN | KEKAKEFFKE | MSSLYGNTPN | VIYEIANEPN |
| K11, | LRDDWGITVF | RAAMYTADGG | YIDNPSVKNK | VKEAVEAAKE | LGIYVIIDWH | ILNDGNPNQN | KEKAKEFFKE | MSSLYGNTPN | VIYEIANEPN |
| Umas | LRDDWGITVF | RAAMYTADGG | YIDNPSVKNK | VKEAVEAAKE | LGIYVIIDWH | ILNDGNPNQN | KEKAKEFFKE | MSSLYGNTPN | VIYEIANEPN |
| Consensus | LRDDWGITVF | RAAMYTADGG | YIDNPSVKNK | VKEAVEaAKE | LGIYVIIDWH | ILNDGNPNQN | KEKAKEFFKE | MSSLYGNTPN | VIYEIANEPN |

|  | 190 | 200 | 210 | 220 | 230 | 240 | 250 | 260 | 270 |
|---|---|---|---|---|---|---|---|---|---|
| B1, | GDVNWKRDIK | PYAEEVISVI | RKNDPDNPII | VGTGTWSQDV | NDAADDQLKD | ANVMYALHFY | AGTHGQSLRD | KANYALSKGA | PIFVTEWGTS |
| DLG, | GDVNWKRDIK | PYAEEVISVI | RKNDPDNIII | VGTGTWSQDV | NDAADDQLKD | ANVMYALHFY | AGTHGQSLRD | KANYALSKGA | PIFVTEWGTS |
| K11, | GDVNWKRDIK | PYAEEVISVI | RKNDPDNIII | VGTGTWSQDV | NDAADDQLKD | ANVMYALHFY | AGTHGQFLRD | KANYALSKGA | PIFVTEWGTS |
| Umas | GDVNWKRDIK | PYAEEVISVI | RKNDPDNIII | VGTGTWSQDV | NDAADDQLKD | ANVMYALHFY | AGTHGQSLRD | KANYALSKGA | PIFVTEWGTS |
| Consensus | GDVNWKRDIK | PYAEEVISVI | RKNDPDNIII | VGTGTWSQDV | NDAADDQIKD | ANVMYALHFY | AGTHGQsLRD | KANYALSKGA | PIFVTEWGTS |

|  | 280 | 290 | 300 | 310 | 320 | 330 | 340 | 350 | 360 |
|---|---|---|---|---|---|---|---|---|---|
| B1, | DASGNGGVFL | DQSREWLNYL | DSKKISWVNW | NLSDKQESSS | ALKPGASKTG | GWPLSDLTAS | GTFVRENIRG | NKDSTKDGPE | TPAQDNPTQE |
| DLG, | DASGNGGVFL | DQSREWLNYL | DSKNISWVNW | NLSDKQESSS | ALKPGASKTG | GWPLTDLTAS | GTFVRENIRG | TKDSTKDVPE | TPAQDNPTQE |
| K11, | DASGNGGVFL | GQSREWLNYL | DSKKISWVNW | NLSDKQESSS | ALKPGASKTG | GWPLTDLTAS | GTFVRENIRG | TKDSTKDGPE | TPAQDNPAQE |
| Umas | DASGNGGVFL | DQSREWLNYL | DSKNISWVNW | NLSDKQESSS | ALKPGASKTG | GWPLTDLTAS | GTFARENIRG | TKGSTKDGPE | TPAQDNPTQE |
| Consensus | DASGNGGVFL | dQSREWLNYL | DSKnISWVNW | NLSDKQESSS | ALKPGASKTG | GWPLtDLTAS | GTFvRENIRG | tKdSTKDgPE | TPAQDNPtQE |

|  | 370 | 380 | 390 | 400 | 410 | 420 | 430 | 440 | 450 |
|---|---|---|---|---|---|---|---|---|---|
| B1, | KGVSVQYKAG | DGSVNSNQIR | PQLHIKNNGN | TTVDLKDVTA | RYWYNAKNKG | QNFDCDYAQI | GCGNLTHKFV | TLHKPKQGAD | TYLELGFKKG |
| DLG, | KGVSVQYKAG | DGRVNSNQIR | PQLHIKNNGN | ATVDLKDVTA | RYWYNVKNKG | QNFDCDYAQM | GCGNLTHKFV | TLHKPKQGAD | TYLELGFKTG |
| K11, | KGVFVQYKAG | DGRVNSNQIR | PQLHIKNNGN | ATVDLKDVTA | RYWYNAKNKG | QNFDCDYAQM | GCGNLTHRFV | TLHKPKKGAD | TYLELGFKTG |
| Umas | KGVSVQYKAG | YGRVNSNQIR | PQLHMKNNGN | TKVDLKGVTA | RYWYNTKNKG | QNFDCDYTQI | GCGNLTHKFV | TLHKPKQDAD | TYLELGFKTG |
| Consensus | KGVSVQYKAG | dGrVNSNQIR | PQLHiKNNGN | ttVDLKdVTA | RYWYN.KNKG | QNFDCDYaQi | GCGNLTHkFV | TLHKPKqgAD | TYLELGFKtG |

|  | 460 | 470 | 480 | 490 | 500 |
|---|---|---|---|---|---|
| B1, | TLSTGASTGN | IQLRLHNDDW | SNYAQSGDYS | FSNQIRLKQR | KSHIH |
| DLG, | TLSPGASTGN | IQLRLHNDDW | SNYAQSGDYS | FFQSNTFKTT | KKITLYHQGK |
| K11, | TLSPGASTGN | IQLRLHNDDW | SNYAQSGHYS | FFQSNTFKTT | KKITLYHQGK |
| Umas | TLSPGASTGN | IQLRLPMMTG | AIMWKATIIP | FSNQIHLKQR | EKSHYISQGK |
| Consensus | TLSpGASTGN | dGrVNSNQIR | s.yaqsg.ys | Fs#qi.lKqr | kksh...qgk |

|  |  |
|---|---|
| B1, |  |
| DLG, | LIWGTEPN |
| K11, | LIWGTEPN |
| Umas | LIWGTEPN |
| Consensus | liwgtepn |

BACILLUS LICHENIFORMIS B1, ALKALOPHILIC ENZYME SOLUTION AND METHOD OF PRODUCING THE SAME

BACKGROUND OF THE INVENTION

1. Field of the Invention

The present invention relates to *Bacillus licheniformis* B1 strain. In particular, the present invention is to produce an enzyme demonstrating optimal activity in alkali condition using *Bacillus licheniformis* B1, so that it can be applied in various fields including production of detergents.

2. Description of the Prior Art

The traditional Korean fermented food 'Chungkookjang' (soup prepared with fermented soybeans) has long been in the center of our attention in Korea as functional food having intestinal-protecting effect and blood circulation improving effect. Chungkookjang is also called Tempeh, Dushi, Kinema, and Natto in different countries. Chungkookjang is soybean fermented soup. During fermentation, microorganisms, enzymes and diverse bioactive materials are newly generated (Lee et al., 1999, Fermentation patterns of Chungkookjang and Kanjang by *Bacillus licheniformis* B1, Kor. J. Microb. 35, 296-301). Fermentation of Chungkookjang is induced by *Bacillus* sp. One of the enzymes included in Chungkookjang is *Bacillus* proteolytic enzyme, which is called nattokinase in Japan, showing fibrinolytic activity in human body (Sumi, H., H. Hamada, K. Nakanishi, and H. Hiratani. 1990. Enhancement of the fibrinolytic-activity in plasma by oral administration of nattokinase. Acta Haematol. 84, 139-143).

It is widely known that Chungkookjang prepared by fermenting soybean includes sticky polyglutamate or protease, but few studies have reported cellulase decomposing carbohydrates in Chungkookjang. Oligosaccharide, generated from the degradation of high molecular carbohydrate, has diverse bioactivities, so it is worthwhile to study the strain and develop a novel method to produce cellulase having very useful properties.

SUMMARY OF THE INVENTION

The present inventors have previously provided *Bacillus licheniformis* B1 strain (KCTC 0755BP) secreting protease and amylase massively and capable of mass-producing biopolymer known as poly glutamate as it grows and a method for preparing Chungkookjang and Kanjang (soy sauce) using the same in Korean Patent No. 10-0368183 (Invention Title: New Strain *Bacillus licheniformis* B1 and Usages Thereof).

After many years of study and effort, the present inventors have confirmed that cellulase decomposing carbohydrate is produced by *Bacillus licheniformis* B1 strain, the Chungkookjang fermenting strain, and further completed the present invention by confirming that the cellulase is β-1,4-glucanase showing optimum activity in alkali condition (pH 10-13).

Therefore, it is an object of the present invention to provide a novel *Bacillus licheniformis* B1 strain producing cellulase demonstrating high activity in alkali pH range. It is another object of the present invention to provide an alkalophilic enzyme solution containing cellulase induced by *Bacillus licheniformis* B1 strain and demonstrating optimal activity in alkali pH range. It is a further an object of the present invention to provide a method for preparing the alkalophilic enzyme solution containing cellulase exhibiting optimum activity in alkali pH range comprising the steps of culturing the strain and centrifugation. It is still further object of the present invention to provide a use of an enzyme which has excellent enzyme activity in alkali condition and is produced by *Bacillus licheniformis* B1 strain.

To achieve the above objects, in the first embodiment of the present invention, the present invention provides *Bacillus licheniformis* B1 strain capable of producing cellulase showing optimal activity in pH range of 10-13. Herein, the *Bacillus licheniformis* B1 is preferably KCTC 0755BP.

In the second embodiment of the present invention, the present invention provides an alkalophilic enzyme solution, which characteristically contains cellulase induced by *Bacillus licheniformis* B1 and shows optimal activity in pH range of 10-13.

Herein, the *Bacillus licheniformis* B1 is preferably KCTC 0755BP. The optimal activity is shown in pH range 10-13, which means the enzyme activity at pH 10-13 is higher than the enzyme activity at pH 3-7, and the enzyme activity at pH 13 reaches at least 80%.

The cellulase herein is preferably β-1,4-glucanase having signal sequence at 10th-38th amino acids in the coding range of amino acid 10 and 460, and having basic amino acid repeat, such as Lys-Arg, in the amino terminal, followed by hydrophobic region.

In the third embodiment of the present invention, the present invention provides a method for preparing an alkalophilic enzyme solution containing cellulase showing optimal activity at pH 10-13, which comprises the following steps; culturing *Bacillus licheniformis* B1 strain by using cellulose as a substrate and obtaining supernatant by centrifugation; and separating a substance of at least 3,000 Da by centrifugation with the supernatant.

Herein, the *Bacillus licheniformis* B1 is preferably KCTC 0755BP. The cellulase herein is preferably β-1,4-glucanase having signal sequence at 10th-38th amino acids in the coding range of amino acid 10 and 460, and having basic amino acid repeat, such as Lys-Arg, in the amino terminal, followed by hydrophobic region. The optimal activity is shown in pH range 10-13, which means the enzyme activity at pH 10-13 is higher than the enzyme activity at pH 3-7, and the enzyme activity at pH 13 reaches at least 80%.

The present invention provides *Bacillus licheniformis* B1 strain producing cellulase having high activity in alkali pH range. The present invention also provides an alkalophilic enzyme solution containing cellulase induced by *Bacillus licheniformis* B1 strain and demonstrating optimal activity in alkali pH range. The present invention further provides a method for preparing the alkalophilic enzyme solution containing cellulase demonstrating optimal activity in alkali pH range, which comprises the steps of culturing the strain and centrifugation.

BRIEF DESCRIPTION OF THE SEQUENCES

SEQ ID NO: 1 is a DNA sequence of *Bacillus licheniformis* strain K11 cellulase gene.

SEQ ID NO: 2 is a DNA sequence of *Bacillus amyloliquefaciens* strain UMAS 1002 endoglucanase A (engA) gene.

SEQ ID NO: 3 is a DNA sequence of *Bacillus subtilis* DLG endo-β-1,4-glucanase gene.

SEQ ID NO: 4 is an amino acid sequence of *Bacillus licheniformis* B1 β-1,4-glucanase of the present invention.

SEQ ID NO: 5 is a forward primer useful according to the present invention.

SEQ ID NO: 6 is a reverse primer useful according to the present invention.

SEQ ID NO: 7 is an amino acid sequence of the deduced amino terminus of the mature form of the B1 β-1,4-glucanase of the present invention.

BRIEF DESCRIPTION OF THE DRAWINGS

The above and other objects, features and advantages of the present invention will become apparent from the following description of preferred embodiments given in conjunction with the accompanying drawings, in which:

FIG. 5 is a schematic diagram illustrating the amino acid sequences of β-1,4-glucanase of *B. licheniformis* B1 strain of the present invention and the conventional β-1,4-glucanases.

DETAILED DESCRIPTION OF THE PREFERRED EMBODIMENT

The preferred embodiments of the present invention are described in detail hereinafter with the attached figures.

The present inventors confirmed that cellulase decomposing carbohydrate was produced by *Bacillus licheniformis* B1, the Chungkookjang fermenting strain, which has long been known to produce protease. And the present inventors further identified the cellulase as β-1,4-glucanase showing optimum activity in alkali pH range (pH 10-13), leading to the completion of this invention.

Thus, the present invention relates to *Bacillus licheniformis* B1 strain producing cellulase having high enzyme activity in alkali pH range. The enzyme produced according to the present invention and the enzyme solution containing the same may be applied in diverse fields including production of detergent or bio-fuel, since the enzyme solution retains excellent enzyme activity in alkali condition.

*Bacillus licheniformis* B1 used in examples and experimental examples of the present invention is KCTC 0755BP, which was applied for a patent by the present inventors under Korean Patent Application No. 2000-18724 and registered under Korean Patent No. 0368183. The said *Bacillus licheniformis* B1 strain was deposited under the terms of the Budapest Treaty at Korean Collection for Type Culture (KCTC), Korean Research Institute of Bioscience and Biotechnology, 111, Gwahangno, Yuseong-gu, Daejeon 305-806, Korea, on Mar. 14, 2000, and assigned accession number KCTC 0755BP.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Alkalophilic Enzyme Solution

*B. licheniformis* B1 was cultured in LB liquid medium supplemented with 1% cellulose as a substrate for 16 hours, followed by centrifugation to obtain supernatant. The supernatant was loaded in a membrane filter of 3,000 Da, followed by centrifugation to separate protein of at least 3,000 Da. The protein of 3,000 Da attached on the filter was dissolved in PBS (phosphate buffered saline, pH 7.0) to prepare alkalophilic enzyme solution of the present invention.

Example 2

Cellulase Production by Alkalophilic Enzyme Solution of the Present Invention

Experimental Example 1

Congo Red Test

*B. licheniformis* B1 was smeared on LB agar medium supplemented with 0.3% (w/v) carboxymethyl cellulose (CMC, Sigma, USA), followed by culture at 37° C. for 14 hours. The cultured plate medium was treated with 0.1% (w/v) Congo red solution, which stood for 30 minutes. Congo red solution was washed off with 1 M NaCl solution and then enzyme activity was measured.

As a result, when *B. licheniformis* B1 was inoculated to the medium containing CMC, CMC was degraded and thus stained with Congo red. The above result indicates that *B. licheniformis* B1 strain secrets cellulase as set forth in SEQ ID NO: 4.

Experimental Example 2

Activity Staining Test

To react with a substrate, 1% (w/v) CMC aqueous solution was used instead of distilled water for SDS-denaturing polyacrylamide gel electrophoresis. After electrophoresis with the enzyme solution prepared in Example 1, the gel was washed with 0.1 M phosphate buffer (pH 7), which stood in 2.5% (v/v) Triton X-100 for 30 minutes at room temperature.

Enzyme-substrate reaction was induced at 40° C. for 4 hours in the same buffer. Staining with 0.1% Congo red solution was performed for 15 minutes, followed by washing with 1 M NaCl. And then active zone was observed.

As a result of activity staining performed to investigate enzyme activity on gel, one active band was detected (data not shown). This result indicates that *B. licheniformis* B1 strain secrets cellulase SEQ ID NO: 4.

Experimental Example 3

TLC Analysis 0.5 ml of the enzyme solution prepared in Example 1 was mixed with 0.5 ml of substrate solution containing 1% CNC, followed by reaction at 40° C. for 24 hours. The reaction mixture was spotted on silica gel 60 TLC plate (Merck, Germany).

Isoamylalcohol:ethanol:ammonia:water (50:60:1:30) was used as a developing solvent. After development, the mixture was dried in the air, to which the mixed solution composed of 4-methoxybenzaldehyde:H2SO4:glacial acetate:ethanol (5:5:1:90) was sprayed, leading to coloring for 10 minutes at 120° C.

Figure 1:
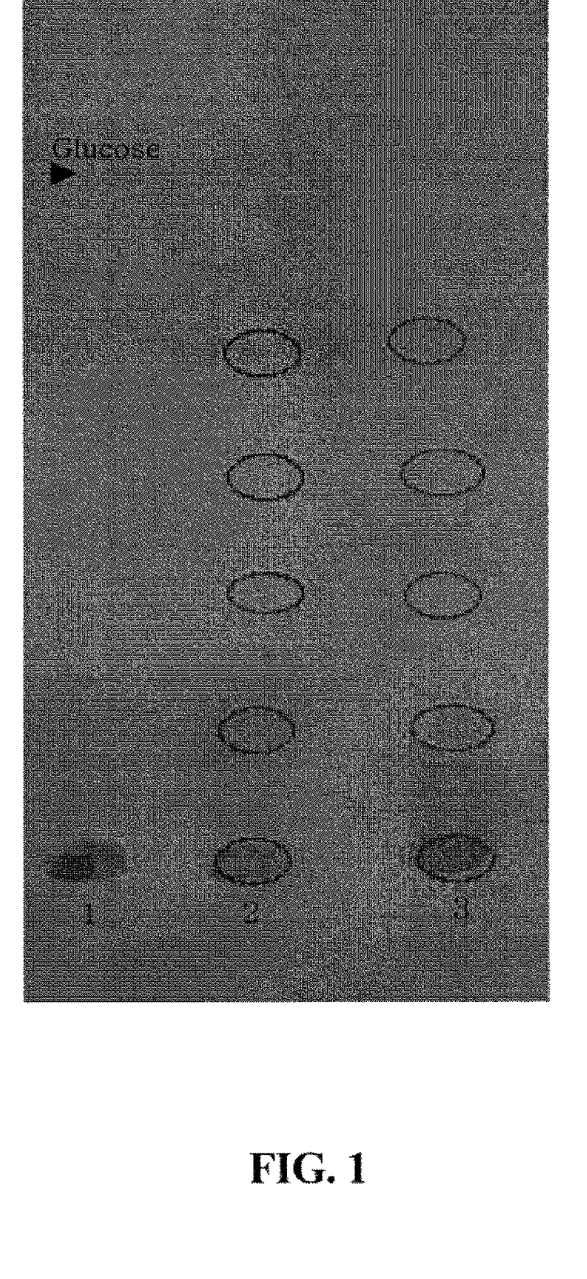
FIG. 1 is a diagram illustrating the result of TLC (thin layer chromatography) with CMC (carboxymethyl cellulose) degraded by the cellulase enzyme solution in a preferred embodiment of the present invention.

FIG. 1 is a diagram illustrating the result of TLC (thin layer chromatography) with CMC (carboxymethyl cellulose) degraded by the cellulase enzyme solution in a preferred embodiment of the present invention (lane 1: CMC was not treated with the enzyme solution of the present invention; lane 2 and 3: The enzyme solution of the present invention was added into 0.1% CMC solution). CMC hydrolyzate produced by the enzyme solution of the present invention was shown under glucose, suggesting that the hydrolyzate was oligosaccharide at least disaccharide (FIG. 1). Considering the capability of degrading CMC, the enzyme solution of the present invention was presumed to contain cellulase.

Example 3

Determination of Optimal PH and Temperature of the Enzyme Solution of the Present Invention Experimental Example 1

Determination of Optimal Ph

Buffers having different pHs were prepared by regulating pH of 0.1 M Tris-Cl with HCl or NaOH. 0.5 ml of the enzyme solution prepared in Example 1 was mixed with 0.5 ml of the substrate solution containing 1% CMC, followed by reaction at 40° C. for one hour at various pHs. OD was measured using DNS (OD550 of the reducing sugar generated by hydrolysis was measured using 3,5-dinitrosalicylic acid (DNS) method).

Figure 2:
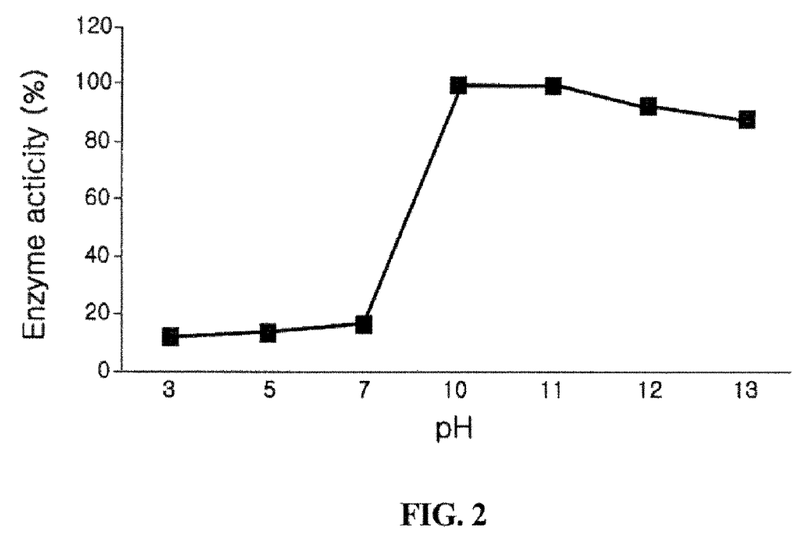
FIG. 2 is a graph illustrating the enzyme activity of cellulase over pH investigated in a preferred embodiment of the present invention.

As a result, as shown in FIG. 2, the enzyme activity was weak up to pH 7, while the highest enzyme activity was observed at pH 10. The enzyme activity remained still high even at higher pH than 10. Some alkalophilic Bacillus β-1,4-glucanases were reported. But, the enzyme of the present invention demonstrated optimal activity at strong alkali (pH 10), and retained its high activity at the strongest alkali condition (pH 13). Again, the enzyme of the present invention demonstrates 80-100% activity in strong alkali condition of pH 10-13, and preferably demonstrates 85-95% activity in that pH range. In particular, the enzyme of the present invention exhibits at least 80% activity at pH 13, and preferably exhibits 80-85% activity at that pH.

Therefore, the enzyme of the present invention can be developed as a detergent. Most detergents so far have been extracted from fungi. However, considering the advantages in the culture of Bacillus strain, the enzyme of the present invention is more effective to produce a detergent than the conventional method to produce a detergent from fungi. Besides, the enzyme of the present invention can be applied in diverse uses requiring high enzyme activity in strong alkali condition, for example in the development of bio-fuel, etc.

Experimental Example 2

Determination of Optimal Temperature 0.1 M Tris-Cl (pH 10) was mixed with 0.5 ml of the substrate solution containing 1% CMC and 0.5 ml of the enzyme solution prepared in Example 1, followed by reaction at various temperatures for one hour. OD was measured using DNS method.

Figure 3:
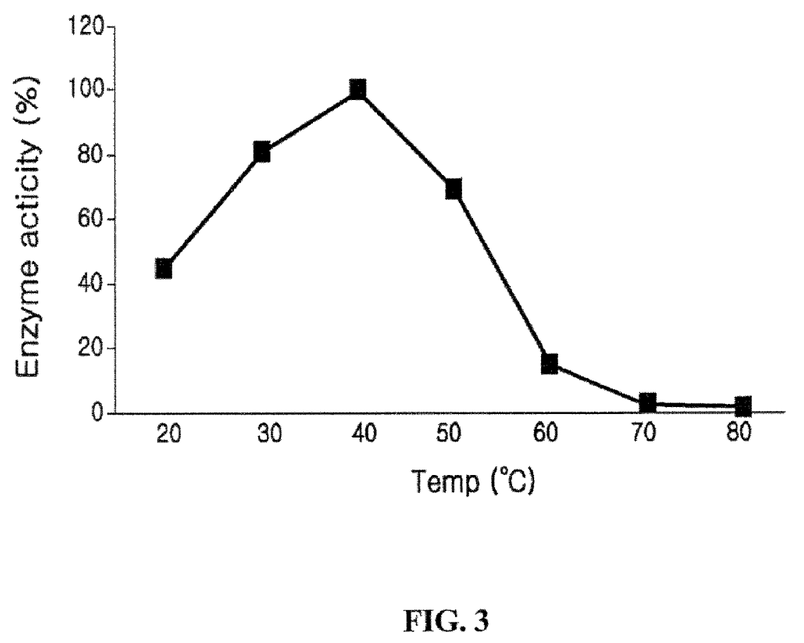
FIG. 3 is a graph illustrating the enzyme activity of cellulase over temperature investigated in a preferred embodiment of the present invention.

As a result, as shown in FIG. 3, the optimal temperature for the enzyme activity was 40° C. At 20° C., 40% of the maximum activity was observed, and at 50° C., 68% of the maximum activity was detected, suggesting that the enzyme had heat-resistance to some degree. However, the enzyme activity was rapidly decreased at the temperature of 60° C. or up.

Example 4

Generation of the Alkalophilic Enzyme of the Present Invention in Chunkookjang and Barley Chungkookjang Bacillus licheniformis B1 was cultured in LB medium at 37° C. for 18 hours and the culture solution was used as a starter. Selected yellow soybeans were added for 18 hours. The culture solution was inoculated to 500 g of soybeans sterilized at 120° C. for 30 minutes or the same but containing 5 g of barely powder (barley Chungkookjang) by 1%. After inoculation, fermentation was induced in a 40° C. incubator.

Figure 4:
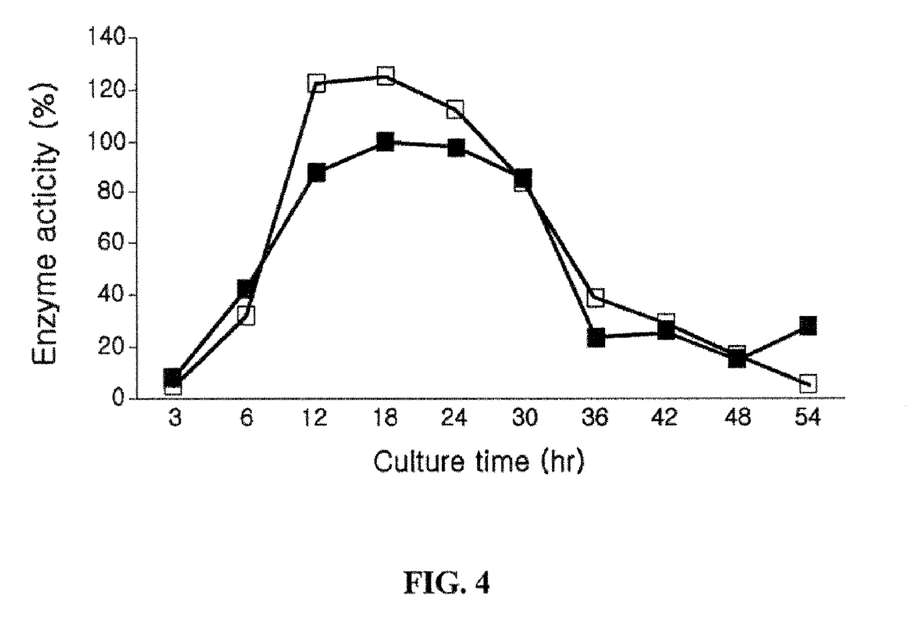
FIG. 4 is a graph illustrating the enzyme activity of cellulase included in Chungkookjang and barley containing Chungkookjang over the culture time.

Chungkookjang fermentation was induced by inoculating soybeans with Bacillus licheniformis B1 strain of the present invention. Some of Chungkookjang was dissolved in water and the supernatant was obtained. DNS decomposition activity of the supernatant was measured. As a result, as shown in FIG. 4, the enzyme activity was increased during 6~30 hour period after culture started. FIG. 4 is a graph illustrating the enzyme activity of cellulase included in Chungkookjang and barley Chungkookjang over the culture time. (The enzyme activity in Chungkookjang: The enzyme activity in Chungkookjang containing barley).

This result suggested that the enzyme of the strain was activated from the 6th hour of the culture. The activation of the enzyme suggests that soybean itself contains a large amount of enzyme substrate. When barley was added to the fermentation of soybean, the enzyme activity was more increased than when soybean alone was fermented (FIG. 4). This result indicates that barley contains a significant amount of enzyme substrate as well. Therefore, β-1,3-bond included in hydrolyzate of barley seems to have immune enhancing effect.

β-glucan in barley endosperm contains glucose as a basic unit and is homopolymer composed of β-1,3-1,4-bond. There are 3 kinds of β-glucanase (β-1,3, β-1,4, and β-1,3-1,4-glucanase). Among these, β-1,3-1,4-glucanase recognizes and cuts β-1,4 bond adjacent to β-1,3 of barley or lichenan. The existence of such enzymes in Chungkookjang fermenting strain was investigated by gene cloning and enzyme activity measurement. As a result, the enzyme in Chungkookjang fermenting strain was identified to be not β-1,3-1,4-glucananse but β-1,4-glucanase (see FIG. 5). So, it was expected that the addition of barley containing β-1,3-bond to Chungkookjang for fermentation could increase immune enhancing effect.

Example 5

Gene Analysis of the Alkalophilic Enzyme of the Present Invention

Figure 6:
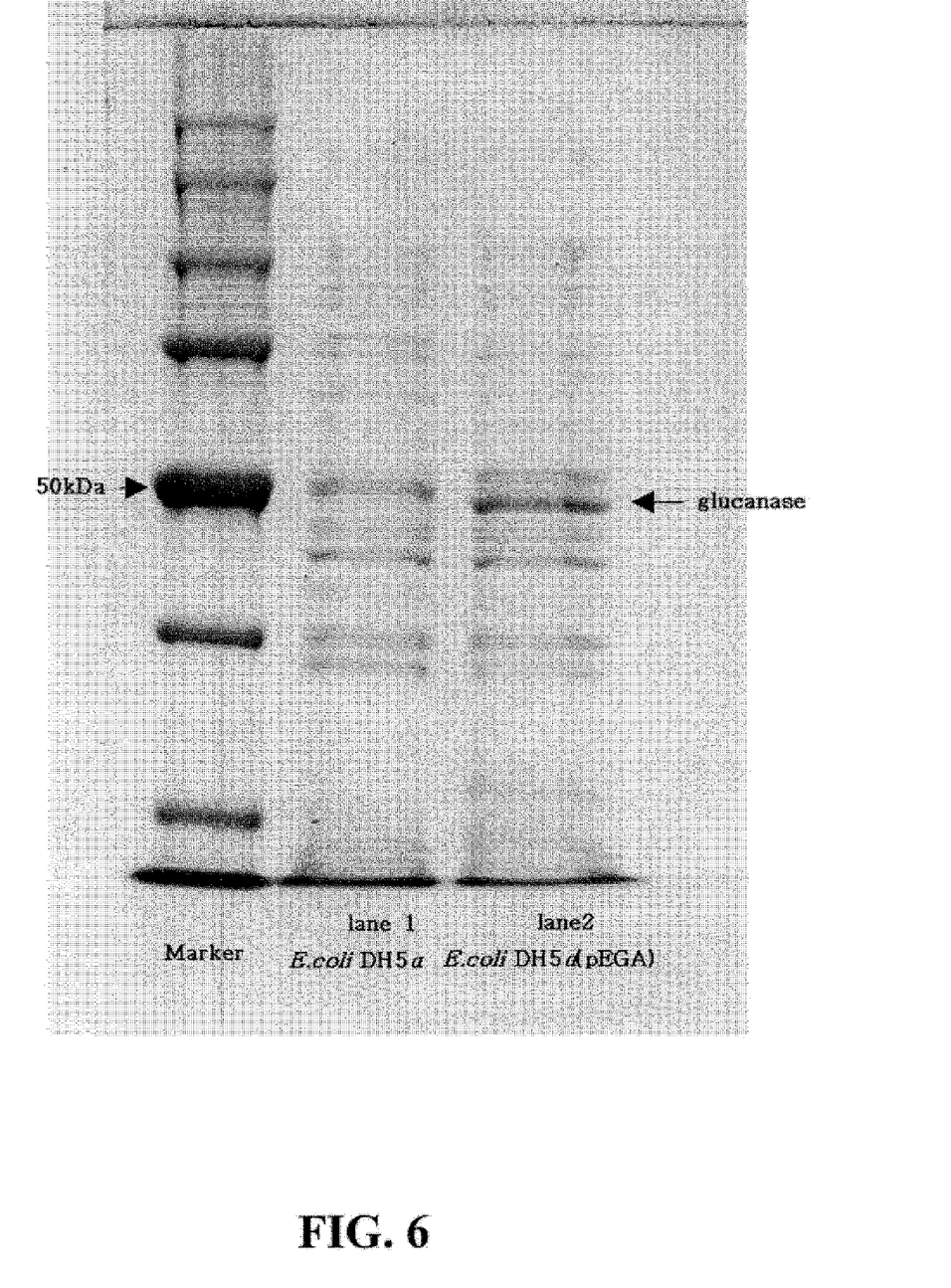
FIG. 6 is a diagram illustrating the result of electrophoresis confirming cellulase (glucanase) of 50 kDa in *E. coli* having the gene cloned according to the present invention.

To clone β-1,4-glucanase, chromosomal DNA of β-1,4-glucanase produced by Bacillus licheniformis B1 according to the method of the present invention was separated and purified. For PCR, a primer set comprising the forward primer, 5'-ATGAAACGGTCAATCTCTAT-3' (SEQ ID NO: 5) and the reverse primer, 5'-CTAATTTGGTTCTGTTC-CCCA-3' (SEQ ID NO: 6) was used. PCR was performed as follows: at 95° C. for 1 minute, at 55° C. for 1 minute, and at 72° C. for 1 minute and 30 seconds (30 cycles). The PCR product was ligated to pGEM-T-EASY vector (Promega, USA) to prepare plasmid. Proteins expressed in *E. coli* and *E. coli* containing the cloned gene were compared by electrophoresis. As shown in FIG. 6, cellulase (glucanase) of 50 kDa was detected in *E. coli* containing the cloned gene only.

Amino acid sequence of β-1,4-glucanase produced by *Bacillus licheniformis* B1 of the present invention was compared with those of *Bacillus licheniformis* strain K11 (cellulase) (GenBank EF070195), *Bacillus amyloliquefaciens* strain UMAS 1002 endoglucanase A (engA) (GenBank AF363635) and *Bacillus subtilis* DLG endo-β-1,4-glucanase (GenBank M16185), as set forth in FIG. 5, by using multiple sequence alignment with hierarchical clustering. The DNA sequences encoding the known enzymes of *Bacillus licheniformis* strain K11(cellulase), *Bacillus amyloliquefaciens* strain UMAS 1002 endoglucanase A (engA), and *Bacillus subtilis* DLG endo-β-1,4-glucanase are set forth in SEQ ID NOs: 1, 2, and 3, respectively.

The cloned cellulase gene was screened by using NCBI BLAST. As a result, as shown in FIG. 5, three β-1,4-glucanase genes encoding proteins having high homology were confirmed. Amino acid sequence of *Bacillus licheniformis* B1 glucanase (B1) was compared with those of *Bacillus licheniformis* strain K11 cellulase (K11), *Bacillus amyloliquefaciens* strain UMAS 1002 endoglucanase A (UMAS) and *Bacillus subtilis* DLG endo-β-1,4-glucanase (DLG).

As a result, the 4 glucanases showed polymorphism at 32 amino acid sites in the $10^{th}$-460th amino acids (see FIG. 5). When *B. licheniformis* B1 and *B. subtilis* DLG were compared, there was difference in polymorphism at 16 sites in the same range (see FIG. 5). When *B. licheniformis* B1 and *B. licheniformis* K11 were compared, there was difference in polymorphism at 20 sites in the same range (see FIG. 5). From the comparison with consensus sequence, it was confirmed that *B. licheniformis* B1 glucanase showed difference at 12 sites but showed no difference at the rest of the range (see FIG. 5). The homology in the amino acid sequence with endo-β-1,4-glucanase (Eg1) of *Bacillus* sp. strain KSM-N252 was investigated and as a result the glucanase of the strain was confirmed to be totally different from Eg1 (data not shown). It was suggested from the comparison with DLG that signal sequence of the endoglucanase contained 10-38 amino acids and was cut behind the upstream of Ala38 of Ala36-Ser-Ala38 and the amino terminal of mature enzyme presumably contained Ala39-Gly-Thr-Lys-Thr-Pro-Val-Ala-Lys471SEQ ID NO: 7). The signal sequence of the enzyme of the present invention contains basic amino acid repeat, such as Lys-Arg, in the amino terminal, followed by hydrophobic region, which is typical characteristics of signal sequence (see FIG. 5). The enzyme activity of *B. subtilis* DLG was outlined in a previous report, but biochemical properties of the rest glucanases have not been reported, yet. In particular, no previous reports said that the optimal pHs for those three β-1,4-glucanases were alkali. Once *B. licheniformis* β-1,4-glucanase gene was cloned, disclosing the regulation mechanism of the expression of the enzyme gene, mass-production of the enzyme, separation and purification of the same and confirmation of biochemical properties thereof could be facilitated.

Cellulase produced by *Bacillus licheniformis* B1 strain of the present invention and the enzyme solution containing the same have excellent enzyme activity in alkali condition, so that they can be effectively applied in diverse uses including the production of detergent or bio-fuel.

What is claimed is:

1. An alkalophilic enzyme solution containing an isolated *Bacillus licheniformis* B1 cellulase, wherein the enzyme activity of said cellulase at pH 13 is at least 80% of the highest enzyme activity observed across the range of pH 10-13.

2. The alkalophilic enzyme solution according to claim 1, wherein the *Bacillus licheniformis* B1 is deposited at the Korean Collection for Type Culture (KCTC) as the strain having accession number KCTC 0755BP.

3. The alkalophilic enzyme solution according to claim 1, wherein the optimal enzyme activity is observed across the range of pH 10-13.

4. The alkalophilic enzyme solution according to claim 1, wherein the cellulase is β-1,4-glucanase, wherein said cellulase comprises a signal peptide comprising the 10th-38th amino acids of SEQ ID NO: 4, and said cellulase has at least one basic amino acid repeat of Lys-Arg in the amino terminal, followed by a hydrophobic region.

5. A method for preparing the alkalophilic enzyme solution containing cellulase showing optimal activity at pH 10-13 according to claim 1, comprising:
    culturing *Bacillus licheniformis* B1 strain by using cellulose as a substrate and obtaining supernatant by centrifugation; and
    separating a substance of at least 3,000 Da by centrifugation with the supernatant.

6. The method for preparing the alkalophilic enzyme solution according to claim 5, wherein the *Bacillus licheniformis* B1 has Korea Collection for Type Culture accession number KCTC 0755BP.

7. The method for preparing the alkalophilic enzyme solution according to claim 5, wherein the cellulase is β-1,4-glucanase comprising the 39$^{th}$-460$^{th}$ amino acids of SEQ ID NO: 4.

8. The method for preparing the alkalophilic enzyme solution according to claim 5, wherein the optimal enzyme activity is observed at pH 10-13, and the enzyme activity at pH 13 is at least 80% of the maximum activity.

9. An alkalophilic enzyme solution containing an isolated cellulase, wherein said cellulase is β-1,4-glucanase comprising the 39th-460th amino acids of SEQ ID NO: 4.

10. The alkalophilic enzyme solution according to claim 9, wherein said cellulase comprises at least one basic amino acid repeat of Lys-Arg in the amino terminal followed by a hydrophobic region.

11. The alkalophilic enzyme solution according to claim 9, wherein said cellulase comprises the 10th-460th amino acids of SEQ ID NO: 4.

12. The alkalophilic enzyme solution according to claim 9, wherein said cellulase comprises the 39th-495th amino acids of SEQ ID NO: 4.

13. The alkalophilic enzyme solution according to claim 9, wherein said cellulase shows optimal activity across the range of pH 10-13.

14. The alkalophilic enzyme solution according to claim 9, wherein the activity of said cellulase at pH 13 is at least 80% of the maximum activity.

15. The alkalophilic enzyme solution according to claim 13, wherein the activity of said cellulase across the range of pH 10-13 is at least 80% of the maximum activity.

16. An isolated cellulase comprising the 39$^{th}$-460$^{th}$ amino acids of SEQ ID NO: 4.

17. The isolated cellulase of claim 16, comprising the 39$^{th}$-495$^{th}$ amino acids of SEQ ID NO: 4.

* * * * *

SEQUENCE LISTING

```
<160> NUMBER OF SEQ ID NOS: 7

<210> SEQ ID NO 1
<211> LENGTH: 1544
<212> TYPE: DNA
<213> ORGANISM: Artificial Sequence
<220> FEATURE:
<223> OTHER INFORMATION: Bacillus licheniformis strain K11

<400> SEQUENCE: 1
aaactttgac tgtgactaca cgcagattgg atgcggcaat ctgacccaca aatttgtgac      60
gctgcataaa cctaagcaag atgcagatac ctatctggaa ctggggttta aaacaggaac     120
gctgtcaccg ggagcaagca cagggaatat tcagcttcgt cttccaatga tgactggagc     180
aattatgcac aaagcgacga ttattccttt ttccaatcaa atacatctaa aacaacgaga     240
aaaatcacat tatatcagtc aaggaaaact gatttgggga acagaaccca attagtaagc     300
tttaggcgga catcagcaac gatgtccgct tttatcatct taaacagcaa tacaaggagg     360
tttacgtggc ggatgaaact ctgaaacagc atatgggcct gtacaaatgt tgttagcaat     420
ctcaagaaag ccaaggagta gatgtgattc actgaacata tgatgtaatg aaaagcgttt     480
gtagcgcaat gtatgtattt cacatccgcc acttttatta cgtaaggggg aacaagagaa     540
tgaaaaagta tgacgcattt ccagagccaa ttggcggcta tactgtcggc cgaacccaga     600
tggattttga gtacacggca tcagatcata caaaaagaga actgacggtg tttgtgtact     660
atccgtccga cagcagcgaa gggaaggcta catcaacgta catgtttcct gaagtctgcg     720
aaatgcttga tgagcagccc gcttctcact gcgttgtgga tggagctcac tcaaactttg     780
```

```
actgtgacta cacgcagatt ggatgcggca atctgaccca caaatttgtg acgctgcata      840
aacctaagca agatgcagat acctatctgg aactggggtt aaaacagga acgctgtcac       900 cgggagcaag cacagggaat attcagcttc gtcttccaat gatgactgga gcaattatgc     960
acaaagcgac gattattcct tttccaatc aaatacatct aaaacaacga gaaaatcac     1020 attatatcag tcaaggaaaa ctgatttggg gaacagaacc caattagtaa gctttaggcg    1080
gacatcagca acgatgtccg cttttatcat cttaaacagc aatacaagga ggtttacgtg    1140
gcggatgaaa ctctgaaaca gcatatgggc ctgtacaaat gttgttagca atctcaagaa    1200
agccaaggag tagatgtgat tcactgaaca tatgatgtaa tgaaaagcgt ttgtagcgca    1260
atgtatgtat ttcacatccg ccacttttat tacgtaaggg ggaacaagag aatgaaaaag   1320
tatgacgcat ttccagagcc aattggcggc tatactgtcg gccgaaccca gatggatttt   1380
gagtacacgg catcagatca tacaaaaaga gaactgacgg tgtttgtgta ctatccgtcc   1440
gacagcagcg aagggaaggc tacatcaacg tacatgtttc ctgaagtctg cgaaatgctt   1500
gatgagcagc ccgcttctca ctgcgttgtg gatggagctc actc                     1544
```

<210> SEQ ID NO 2
<211> LENGTH: 2151
<212> TYPE: DNA
<213> ORGANISM: Artificial Sequence
<220> FEATURE:
<223> OTHER INFORMATION: Bacillus amyloliquefaciens strain UMAS1002

<400> SEQUENCE: 2

```
ctcagtcgac tcatgtgtgt cttattcaat agagatagag caaattgaca ggcttttaca       60
cctctcaaaa acaagaaatt aggttgatag acaatcatga gaaagatttt tacaatgagt      120
tcgagctcat aagaagtgaa gagccaaaat gatgcgaagg aggaaaagat cagatatgaa     180
acggtcaatt tctatttta ttacgtgttt attgattgcg gtattgacaa tgggcggctt       240
gctgccttcg ccggcatctg cagcagggac aaaaacgcca gtagccaaga atggtcagct     300
tagcataaaa gatacacaac tcgtaaaccg agacggcaaa gcggtacaac tgaaagggat    360
cagttcacat ggattgcaat ggtatggcga tttcgtcaat aaagacagct taaaatggct    420
gagagacgat tggggcatca ccgttttccg cgcggcgatg tatacggcag atggcggtta    480
tattgacaac ccgtccgtga aaaataaagt aaaagaagcg gttgaagcgg caaaagaact    540
tgggatatat gtcatcattg actggcatat cttaaatgac ggcaacccaa accaaaataa    600
agagaaggca aaagaatttt tcaaggagat gtcaagtctt tacggaaaca cgccaaacgt    660
catttatgaa attgcaaacg aaccaaacgg tgacgtgaac tggaagcgtg atattaaacc    720
gtatgcagaa gaagtgattt ccgttatccg caaaaatgat ccagcaacaa tcatcattgt    780
cggaaccggt acatggagcc aggatgtgaa tgatgctgca gatgatcagc taaaagatgc    840
aaacgtcatg tacgcgcttc atttttatgc cggcacacac ggccaatctt tacgggataa    900
agcaaactat gcactcagta aaggagcgcc tatttcgtg acggaatggg gaacaagcga    960
tgcgtctgga aatggcggtg tattccttga ccaatcgcgg gaatggctga attatctcga   1020
cagcaagaac atcagctggg tgaactggaa tctttctgat aagcaggaat catcctcggc   1080
tttaaagccg ggagcatcta aaacaggcgg ctggccgctt acagatttaa ctgcttcagg   1140
aacattcgca agagaaaaca ttcgcggtac caaaggttcg cgaaggacgg ccctgaaacg   1200
ccagcacaag ataaccccac acaggaaaaa ggcgttttctg tacaatacaa agcagggtat    1260
gggcgtgtga acagcaatca aatccgcccg cagcttcaca tgaaaaataa cgggaatacc    1320
```

-continued

```
aaggttgatt taaaaggtgt cactgcccgt tactggtata acacgaaaaa caaaggccaa    1380
aactttgact gtgactacac gcagattgga tgcggcaatc tgacccacaa atttgtgacg    1440
ctgcataaac ctaagcaaga tgcagatacc tatctggaac tggggtttaa aacaggaacg    1500
ctgtcaccgg gagcaagcac agggaatatt cagcttcgtc ttccaatgat gactggagca    1560
attatgcaca aagcgacgat tattccttt tccaatcaaa tacatctaaa acaacgagaa     1620
aaatcacatt atatcagtca aggaaaactg atttggggaa cagaacccaa ttagtaagct    1680
ttaggcggac atcagcaacg atgtccgctt ttatcatctt aaacagcaat acaaggaggt    1740
ttacgtggcg gatgaaactc tgaaacagca tatgggcctg tacaaatgtt gttagcaatc    1800
tcaagaaagc caaggagtag atgtgattca ctgaacatat gatgtaatga aaagcgtttg    1860
tagcgcaatg tatgtatttc acatccgcca ctttattac gtaaggggga acaagagaat     1920
gaaaaagtat gacgcatttc cagagccaat ggcggctat actgtcggcc gaacccagat     1980
ggattttgag tacacggcat cagatcatac aaaaagagaa ctgacggtgt ttgtgtacta    2040
tccgtccgac agcagcgaag ggaaggctac atcaacgtac atgtttcctg aagtctgcga    2100
aatgcttgat gagcagcccg cttctcactg cgttgtggat ggagctcact c             2151
```

<210> SEQ ID NO 3
<211> LENGTH: 1920
<212> TYPE: DNA
<213> ORGANISM: Artificial Sequence
<220> FEATURE:
<223> OTHER INFORMATION: Bacillus subtilis DLG

<400> SEQUENCE: 3

```
ttctggctga atccctcact gaagtacaat cttattgtac aactccaacc ttaacccgta      60
ttaatccgaa ccttacatca accttaaatt aacaaggact cgtcttctta cagcaatcat     120
aagattcaat gccatattga gactcatcac attcagcgtg tctacgttgg aaatacattt     180
aattttcga ttcgattgaa aaatgacgtg taaagtcccg attcagcccg gttttctttg      240
ttctatatgt gtcaggtgtg tcttattcaa tagagataga gcaaattgac aggcttttac     300
acctcccaaa aacaagaaat taggttgata gacaatcatg agaaagattt ttacaatgag     360
ttcgagctca taagaaagag ccaaaatgat gcgaaggagg aaaagatcag atatgaaacg     420
gtcaatttct attttattta cgtgtttatt gattgcggta ttgacaatgg gcggcttgct     480
gccttcgccg gcatcagcag cagggacaaa acgccagta gccaagaatg gtcagcttag     540
cataaaaggt acacagctcg taaaccgaga cggcaaagcg gtacaactga aagggatcag     600
ttcacatgga ttgcaatggt atggcgattt cgtcaataaa gacagcttaa atggctgag     660
agacgattgg ggcataaccg ttttccgcgc tgcgatgtat acggcagatg gcggttatat     720
tgacaacccg tccgtgaaaa ataaagtaaa agaagcggtt gaagcggcaa agaacttgg     780
gatatatgtc atcattgact ggcatatttt aaatgacggc aacccaaacc aaaataaaga     840
gaaggcaaaa gaattttca aggagatgtc aagtctttac ggaaacacgc caaacgtcat     900
ttatgaaatt gcaaacgaac caaacggtga cgtgaactgg aagcgtgata ttaaaccgta     960
tgcggaagaa gtgatttccg ttatccgcaa aaatgatcca gacaacatca tcattgtcgg    1020
caccggtaca tggagccaag atgtgaatga tgcagccgat gatcagctaa agatgcaaa     1080
cgtcatgtac gcgcttcatt tttatgccgg cacacatggc caatctttac gggataaagc    1140
aaactatgca ctcagtaaag gagcgcctat tttcgtgacg gaatggggaa caagcgacgc    1200
gtctggaaat ggcggtgtat tccttgacca gtcgcgggaa tggctgaatt atctcgacag    1260
```

-continued

```
taagaacatc agctgggtga actggaatct ttctgataag caggaatcat cttcggcttt    1320
aaagccggga gcatctaaaa caggcggctg gccgcttaca gatttaactg cttcaggaac    1380
attcgtaaga gaaacattc gcggcactaa agattcgacg aaggacgtcc ctgaaacgcc     1440
agcacaagat aaccccacac aggaaaaagg cgtttctgta caatacaaag caggggatgg    1500
gcgtgtgaac agcaatcaaa tccgcccgca gcttcacata aaaataacg gcaatgcgac     1560 ggttgattta aaagatgtca ctgcccgtta ctggtataac gtgaaaaaca aaggccaaaa    1620
ctttgactgt gactacgcgc agatgggatg cggcaatctg acccacaagt tgtgacgct     1680 gcataaacct aagcaaggtg cagatacccta tctggaactg gggtttaaaa caggaacgct   1740
gtcaccggga gcaagcacag ggaatattca gcttcgtctt cacaatgatg actggagcaa    1800
ttatgcacaa agcggcgatt attccttttt ccaatcaaat acgtttaaaa caacgaaaaa    1860
aatcacatta tatcatcaag gaaaactgat ttggggaaca gaacccaatt agttaagctt    1920
```

<210> SEQ ID NO 4
<211> LENGTH: 495
<212> TYPE: PRT
<213> ORGANISM: Artificial Sequence
<220> FEATURE:
<223> OTHER INFORMATION: Bacillus licheniformis strain B1

<400> SEQUENCE: 4

```
Met Met Arg Arg Arg Lys Arg Ser Asp Met Lys Arg Ser Ile Ser Ile
1               5                   10                  15

Phe Ile Thr Cys Leu Leu Ile Thr Val Leu Thr Met Ser Gly Leu Pro
            20                  25                  30

Ala Ser Pro Ala Ser Ala Ala Gly Thr Lys Thr Pro Val Ala Lys Asn
        35                  40                  45

Gly Gln Leu Ser Ile Lys Gly Thr Gln Leu Val Asn Arg Asp Gly Lys
    50                  55                  60

Ala Ile Gln Leu Lys Gly Ile Ser Ser His Gly Leu Gln Trp Tyr Gly
65                  70                  75                  80

Asp Phe Val Asn Lys Asp Ser Leu Lys Trp Leu Arg Asp Asp Trp Gly
                85                  90                  95

Ile Thr Val Phe Arg Ala Ala Met Tyr Thr Ala Asp Gly Gly Tyr Ile
            100                 105                 110

Asp Asn Pro Ser Val Lys Asn Lys Val Lys Glu Ala Val Glu Thr Ala
        115                 120                 125

Lys Glu Leu Gly Ile Tyr Val Ile Ile Asp Trp His Ile Leu Asn Asp
    130                 135                 140

Gly Asn Pro Asn Gln Asn Lys Glu Lys Ala Lys Glu Phe Phe Lys Glu
145                 150                 155                 160

Met Ser Ser Leu Tyr Gly Asn Thr Pro Asn Val Ile Tyr Glu Ile Ala
                165                 170                 175

Asn Glu Pro Asn Gly Asp Val Asn Trp Lys Arg Asp Ile Lys Pro Tyr
            180                 185                 190

Ala Glu Glu Val Ile Ser Val Ile Arg Lys Asn Asp Pro Asp Asn Pro
        195                 200                 205

Ile Ile Val Gly Thr Gly Thr Trp Ser Gln Asp Val Asn Asp Ala Ala
    210                 215                 220

Asp Asp Gln Leu Lys Asp Ala Asn Val Met Tyr Ala Leu His Phe Tyr
225                 230                 235                 240

Ala Gly Thr His Gly Gln Ser Leu Arg Asp Lys Ala Asn Tyr Ala Leu
                245                 250                 255
```

```
Ser Lys Gly Ala Pro Ile Phe Val Thr Glu Trp Thr Ser Asp Ala
            260                 265                 270
Ser Gly Asn Gly Gly Val Phe Leu Asp Gln Ser Arg Glu Trp Leu Asn
        275                 280                 285
Tyr Leu Asp Ser Lys Lys Ile Ser Trp Val Asn Trp Asn Leu Ser Asp
        290                 295                 300
Lys Gln Glu Ser Ser Ala Leu Lys Pro Gly Ala Ser Lys Thr Gly
305                 310                 315                 320
Gly Trp Pro Leu Ser Asp Leu Thr Ala Ser Gly Thr Phe Val Arg Glu
                325                 330                 335
Asn Ile Arg Gly Asn Lys Asp Ser Thr Lys Asp Gly Pro Glu Thr Pro
            340                 345                 350
Ala Gln Asp Asn Pro Thr Gln Glu Lys Gly Val Ser Val Gln Tyr Lys
        355                 360                 365
Ala Gly Asp Gly Ser Val Asn Ser Asn Gln Ile Arg Pro Gln Leu His
        370                 375                 380
Ile Lys Asn Asn Gly Asn Thr Thr Val Asp Leu Lys Asp Val Thr Ala
385                 390                 395                 400
Arg Tyr Trp Tyr Asn Ala Lys Asn Lys Gly Gln Asn Phe Asp Cys Asp
                405                 410                 415
Tyr Ala Gln Ile Gly Cys Gly Asn Leu Thr His Lys Phe Val Thr Leu
            420                 425                 430
His Lys Pro Lys Gln Gly Ala Asp Thr Tyr Leu Glu Leu Gly Phe Lys
        435                 440                 445
Lys Gly Thr Leu Ser Thr Gly Ala Ser Thr Gly Asn Ile Gln Leu Arg
        450                 455                 460
Leu His Asn Asp Asp Trp Ser Asn Tyr Ala Gln Ser Gly Asp Tyr Ser
465                 470                 475                 480
Phe Ser Asn Gln Ile Arg Leu Lys Gln Arg Lys Ser His Ile His
                485                 490                 495

<210> SEQ ID NO 5
<211> LENGTH: 20
<212> TYPE: DNA
<213> ORGANISM: Artificial Sequence
<220> FEATURE:
<223> OTHER INFORMATION: Forward Primer

<400> SEQUENCE: 5
atgaaacggt caatctctat                                          20

<210> SEQ ID NO 6
<211> LENGTH: 21
<212> TYPE: DNA
<213> ORGANISM: Artificial Sequence
<220> FEATURE:
<223> OTHER INFORMATION: Reverse Primer

<400> SEQUENCE: 6
ctaatttggt tctgttcccc a                                        21

<210> SEQ ID NO 7
<211> LENGTH: 26
<212> TYPE: PRT
<213> ORGANISM: Artificial Sequence
<220> FEATURE:
<223> OTHER INFORMATION: Bacillus licheniformis B1

<400> SEQUENCE: 7

Ala Leu Ala Gly Leu Tyr Thr His Arg Leu Tyr Ser Thr His Arg Pro
```

```
                1               5              10              15
Arg Val Ala Leu Ala Leu Ala Leu Tyr Ser
                               20              25
```